United States Patent
McGreevy et al.

(10) Patent No.: US 7,678,105 B2
(45) Date of Patent: Mar. 16, 2010

(54) METHOD AND APPARATUS FOR PRECURSIVELY CONTROLLING ENERGY DURING COAPTIVE TISSUE FUSION

(75) Inventors: Francis T. McGreevy, Aurora, CO (US); Katherine R. Pavlovsky, Littleton, CO (US)

(73) Assignee: ConMed Corporation, Utica, NY (US)

( * ) Notice: Subject to any disclaimer, the term of this patent is extended or adjusted under 35 U.S.C. 154(b) by 777 days.

(21) Appl. No.: 11/228,891

(22) Filed: Sep. 16, 2005

(65) Prior Publication Data

US 2007/0066969 A1 Mar. 22, 2007

(51) Int. Cl.
*A61B 18/14* (2006.01)
(52) U.S. Cl. .............................. 606/32; 606/51; 606/40; 606/41
(58) Field of Classification Search .............. 606/32–52
See application file for complete search history.

(56) References Cited

U.S. PATENT DOCUMENTS

| | | | |
|---|---|---|---|
| 4,658,819 A | 4/1987 | Harris et al. | |
| 4,860,745 A | 8/1989 | Farin et al. | |
| 5,370,645 A | 12/1994 | Klicek et al. | |
| 5,403,312 A | 4/1995 | Yates et al. | |
| 5,422,567 A | 6/1995 | Matsunaga | |
| 5,437,664 A | 8/1995 | Cohen et al. | |
| 5,443,463 A | 8/1995 | Stern et al. | |
| 5,514,129 A | 5/1996 | Smith | |
| 5,540,684 A | 7/1996 | Hassler, Jr. | |
| 5,558,671 A | 9/1996 | Yates | |
| 5,599,344 A | 2/1997 | Paterson | |
| 5,720,744 A | 2/1998 | Eggleston et al. | |
| 5,817,093 A | 10/1998 | Williamson, IV et al. | |
| 5,827,271 A | 10/1998 | Buysse et al. | |
| 6,010,516 A | 1/2000 | Hulka | |
| 6,033,399 A | 3/2000 | Gines | |
| 6,083,223 A | 7/2000 | Baker | |
| 6,142,992 A | 11/2000 | Cheng et al. | |
| 6,203,541 B1 | 3/2001 | Keppel | |
| 6,210,403 B1 | 4/2001 | Klicek | |
| 6,228,080 B1 | 5/2001 | Gines | |
| 6,261,286 B1 | 7/2001 | Goble et al. | |
| 6,267,761 B1 | 7/2001 | Ryan | |
| 6,270,497 B1 | 8/2001 | Sekino et al. | |

(Continued)

OTHER PUBLICATIONS

Physical Factors in Electrocoaptation of Blood Vessels. By Bernard Sigel and Fred L. Hathe, Arch Surg; vol. 95, p. 54-58, Jul. 1967.

(Continued)

*Primary Examiner*—Michael Peffley
*Assistant Examiner*—Ronald Hupczey, Jr.
(74) *Attorney, Agent, or Firm*—John R. Ley

(57) ABSTRACT

A sidewall of biological tissue which surrounds and defines an opening in the tissue is sealed or fused to occlude the opening by compressing apposite sidewall portions and applying sufficient energy to cause the fibers of the compressed apposed sidewall portions to intertwine and fuse with one another to form a permanent seal. The energy application is controlled by detecting a precursor fusion condition while applying the energy and before sufficient energy has been applied to achieve an adequate seal. The application of energy is terminated in a time-delayed relationship to the detection of the precursor fusion condition such that sufficient energy has been applied to achieve an effective seal. The precursor fusion condition is detected upon the peak RF current delivered to the tissue remaining below a threshold value for a threshold time.

26 Claims, 9 Drawing Sheets

U.S. PATENT DOCUMENTS

| | | | |
|---|---|---|---|
| 6,358,246 | B1 | 3/2002 | Behl et al. |
| 6,398,779 | B1 | 6/2002 | Buysse et al. |
| 6,562,037 | B2 | 5/2003 | Paton et al. |
| 6,733,498 | B2 | 5/2004 | Paton et al. |
| 7,367,972 | B2 * | 5/2008 | Francischelli et al. ......... 606/34 |
| 2001/0039417 | A1 * | 11/2001 | Harano et al. ................. 606/40 |
| 2003/0114845 | A1 | 6/2003 | Paton et al. |
| 2004/0068304 | A1 | 4/2004 | Paton et al. |

OTHER PUBLICATIONS

Electrosurgical Tissue Resection: A Numerical and Experimental Study. By Dmitriy E. Protsenko and John A. Pearce, Proceedings of SPIE vol. 4954, p. 64-70 (2003).

Evaluation of a Vessel Sealing System, Bipolar Electrosurgery, Harmonic Scalpel, Titanium Clips, Endoscopic Gastrointestinal Anastomosis Vascular Staples and Sutures for Arterial and Venous Ligation in a Porcine Model. By Landman, Kerbl, Rehman, Andreoni, Humphrey, Collyer, Olweny, Sundaram and Clayman. Journal of Urology, vol. 169, 697-700, Feb. 2003.

Automatically Controlled Bipolar Electrocoagulation—"COA-COMP." By Bertil Vallfors and Bjorn Bergdahl. Neurosurg. Rev. 7, 187-189 (1984).

"Coa-Comp"—Computerized Automatic Bipolar Electrocoagulation for Neurosurgery and Precision Surgery. By Vallfors, B., Bergdahl, B. Acta Neurochirugica V. 66 n. 3/4 1982 p. 256.

* cited by examiner

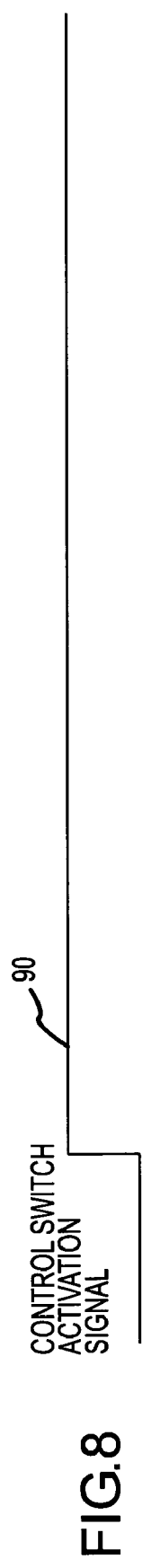
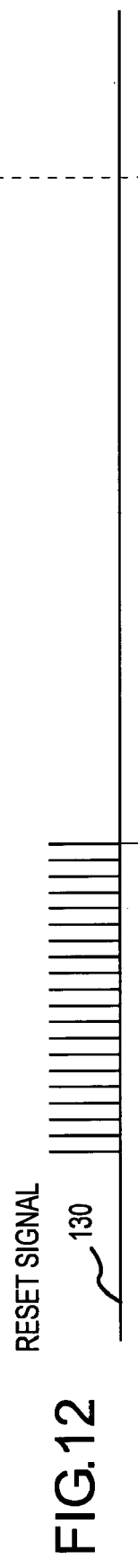
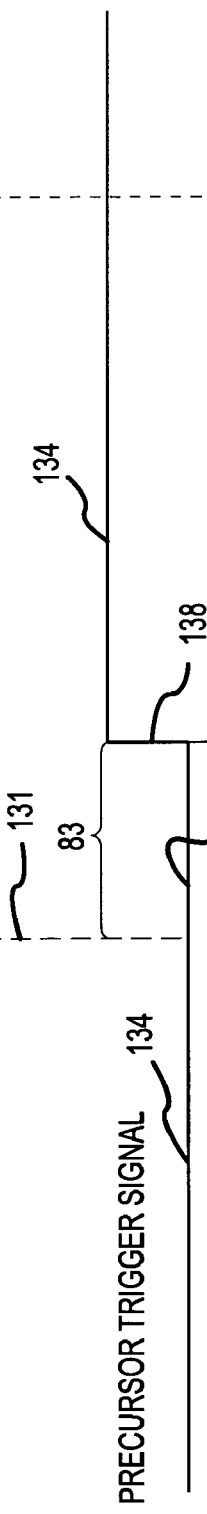
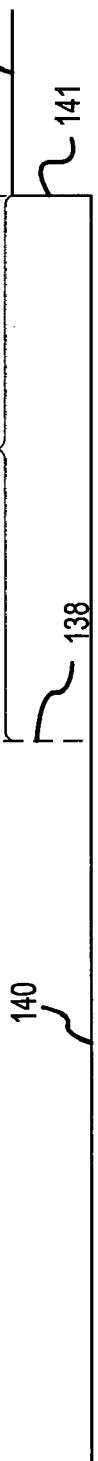
FIG.8 CONTROL SWITCH ACTIVATION SIGNAL 90
FIG.9 RELAY CONTROL SIGNAL 144
FIG.12 RESET SIGNAL 130
FIG.13 PRECURSOR TRIGGER SIGNAL 134
FIG.14 TERMINATION SIGNAL 140

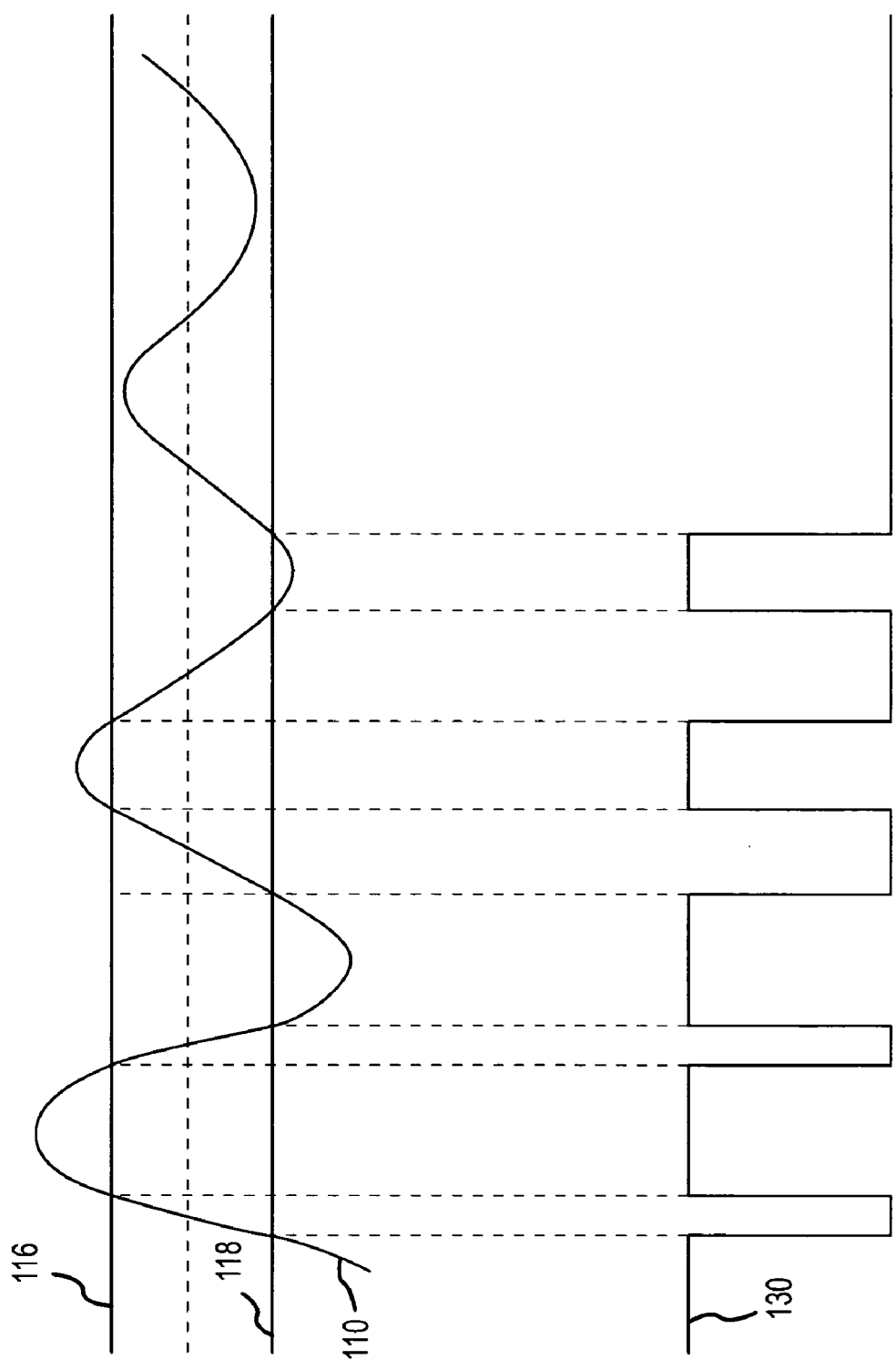

METHOD AND APPARATUS FOR PRECURSIVELY CONTROLLING ENERGY DURING COAPTIVE TISSUE FUSION

The present invention relates to fusing or sealing biological tissue to permanently occlude a lumen, duct, passageway or chamber formed in and surrounded by the tissue. More particularly, the present invention relates to a new and improved coaptive sealing apparatus and method which straightforwardly controls the energy applied to the tissue based on a precursive fusion condition to reliably and rapidly achieve an effective seal, without the use of complicated, expensive and ineffective energy control and feedback techniques.

BACKGROUND OF THE INVENTION

Tissue fusion has been used in medical procedures for many decades, primarily to prevent bleeding from severed blood vessels. One age-old technique of fusing tissue involves heat application to cauterize vessels. More recent techniques involve the application of electrosurgical electrical energy to tissue to create the heat necessary for tissue fusion. The electrical energy may be applied in an obliterative or a coaptive manner.

Obliterative tissue fusion involves applying electrosurgical energy to the open vessel. The heat created by the electrical energy shrinks and constricts the blood vessel, and blood coagulation contributes to occluding the vessel. Generally speaking, obliterative tissue fusion is primarily useful on relatively small vessels. In electrosurgery, obliterative tissue fusion occurs during standard coagulation and spray coagulation. Obliterative tissue fusion on larger vessels is regarded as less reliable, and therefore poses more risks of internal bleeding after the surgery has been completed. For this and other reasons, coaptive electrosurgical tissue fusion, or some other type of tissue sealing and closure technique, such as mechanical ligature, is generally regarded as more favorable and reliable for larger vessels.

Coaptive electrosurgical tissue fusion involves physical apposition and compression of the tissue which surrounds the lumen, duct, passageway or chamber to be sealed, followed by heating the compressed apposed tissue portions. Usually the source of heat is electrical energy, which is either conducted through the tissue or is conducted through a heating element that is placed in contact with the tissue. One well-known and relatively old technique of coaptive electrosurgical tissue fusion involves grasping the vessel with a hemostat (a scissors-like clamping device) and conducting electrosurgical energy through the hemostat to the tissue. More recent coaptive electrosurgical tissue fusion devices use a specifically-configured handpiece with jaws that clamp around and compress the vessel while a controlled and regulated amount of electrical current is applied to electrodes within the jaws to heat the tissue. Radio frequency (RF) energy is used primarily to create the heating effects, because the tissue may conduct the current and RF currents minimally stimulate the nervous system if at all. Other known sources of heating energy include direct current (DC) applied to resistive heating elements, ultrasound which vibrates the tissue to generate heat, microwaves which interact with the molecular structure of the tissue to generate heat, and light which transfers energy to the cellular components of the tissue, among others.

In coaptive tissue fusion, it is very important to control the amount of energy delivered to the tissue to achieve an effective seal or fusion of the tissue. An effective seal is one which is capable of withstanding leaks caused by the blood pressure and other stresses and pressures from the fluid within the occluded lumen, duct, passageway or chamber. Applying too much energy to the tissue may destroy or denature the tissue to the point where collagen and elastin fibers within the tissue are incapable of fusing and intertwining in such a way to achieve an effective seal. Intertwining and fusing the fibers within the tissue of the two apposite tissue portions is believed to be the primary mechanism for fusing and sealing the tissue. Applying too much energy may obliterate the tissue or destroy or compromise the ability of the fibers to loosen and unwind and thereafter tangle, intertwine and fuse in new tissue masses to join the previously separate apposed tissues. Applying too little energy to the tissue will not increase the flexibility of the fibers to the point where they will loosen enough to interact and fuse sufficiently with the fibers of the apposite tissue.

In those prior art tissue sealing devices such as the hemostat, the application of the electrical energy to the tissue is not specifically controlled but is instead left to the surgeon to determine when enough heat has been applied. Determining when enough heat energy has been applied is particularly difficult if not impossible, because different tissues respond differently. Determining whether a seal is effective by simple observation is impossible. Therefore, most modern coaptive tissue sealing devices attempt to control the application of energy automatically to achieve an effective seal.

Modern coaptive tissue sealing devices typically use complex functional components for measuring and calculating tissue impedance, tissue temperature and other physical tissue parameters to determine and control the amount of energy applied. Most of these devices include feedback control loops which depend on the values of these tissue parameters to adjust the energy delivered to the tissue. In most cases, these tissue parameters are calculated based on measurements of the voltage and current applied to the tissue. Calculations based on the measurements of the voltage and current must thereafter be performed, and the calculated values used in the feedback control loops and other power delivery functionality of the devices. The ability of such prior art tissue sealing devices is therefore subject to a number of complex constraints, including the accuracy of sensing the values and the tissue parameters, the speed and reliability of making the calculations, and the ability of the components of the device to respond. Consequently, most modern coaptive tissue sealing devices are relatively complex in their functionality and relatively expensive because of their complex functionality.

Examples of these types of prior art tissue sealing devices are those which respond to a measured, fixed or variable impedance level occurring while heating the tissue to indicate that the seal is complete. Upon achieving this impedance level, the delivery of electrical energy to the tissue is terminated. Detecting impedance can be computationally intensive and time consuming, thereby delaying the calculated value of the tissue impedance relative to the actual value of the tissue impedance at the time that the calculation is made available. Detecting impedance can be virtually impossible under conditions where the electrical energy is arcing between the jaws which grasp the tissue. Arcing at the ending stages of the tissue sealing process is prevalent in prior art RF tissue sealing devices. Consequently, using an impedance value to establish the point for terminating the delivery of RF electrical energy to the tissue makes it very difficult or impossible to achieve optimum sealing conditions.

Other types of prior art tissue sealing devices determine the impedance level while modulating the electrical energy delivered to the tissue. Modulating the electrical energy delivered is intended to prevent overheating of the tissue, and in that sense is an implicit recognition of the slow response of the feedback control system in regulating the output energy delivered to the tissue. Moreover, modulating the electrical energy delivered while simultaneously calculating impedance and other control parameters increases the complexity of the equipment required.

Still other types of prior art tissue sealing devices automatically reduce the electrosurgical power delivered throughout the tissue sealing event to reduce tissue charring, and then terminate the energy delivery when the current drops below a certain level. Reducing the energy delivery rate extends the time required to achieve an adequate seal, and may therefore result in greater thermal damage to the tissue because of the prolonged heat application time.

Because of the variable and uncertain effects from most prior art tissue sealing devices, surgeons are frequently prone to perform multiple seals on the same vessel, in an attempt to assure that one of these seals will be effective. Performing multiple seats on the same vessel is time-consuming. Upwards of 20 seconds of time may be required to accomplish each seal. The number of seals necessary to be performed in a surgical operation can vary according to the type of operation, but the use of a tissue sealing device in surgery usually occurs under circumstances where the surgeon has judged that the procedure will be more efficiently performed by using a tissue sealing device compared to using an alternative tissue sealing technique such as mechanical ligature. Accordingly and in addition to the requirement for permanent and leak-free seals, the speed at which the tissue sealing device accomplishes the seal is very important. Minimizing the time required to achieve effective seals diminishes the time of the surgical procedure and therefore minimizes risks associated with the procedure.

SUMMARY OF THE INVENTION

The present invention fuses and seals tissue by determining a straightforward precursor fusion condition during the progress of the tissue sealing procedure. The precursor fusion condition establishes the conditions for terminating the delivery of electrical energy. The precursor fusion condition is relatively easily sensed and determined, and the precursor condition is used in a straightforward manner to control energy application without requiring complex calculations, feedback power control loops, or energy modulation techniques. Furthermore, even though the precursor fusion condition is not predictably and reliably related to tissue impedance, the precursor fusion condition nevertheless predicts conditions under which a very effective seal is achieved in different types of tissues. The present invention permits a prior art electrosurgical generator and a prior art tissue sealing handpiece to be used together as a tissue fusion apparatus, thereby avoiding the necessity to use a separate and expensive energy generator designed specifically for tissue sealing purposes. Tissue seals which are equally or more effective are typically obtained in considerably shorter times, compared to those tissue seals obtained by known and commercially available prior art tissue sealing devices.

One aspect of the present invention involves a method of coaptively sealing a sidewall of biological tissue which surrounds and defines an opening in the tissue to occlude the opening. The tissue of the sidewall includes biological fibers. The method involves compressing portions of the sidewall in apposition to occlude the opening, applying sufficient energy to the compressed apposed sidewall portions to cause the fibers of the compressed apposed sidewall portions to intertwine and fuse with one another to a sufficient degree to hold the apposed sidewall portions permanently together and occlude the opening permanently, detecting a precursor fusion condition while applying the energy to the compressed apposite sidewall portions and before sufficient energy has been applied to cause the fibers to intertwine and fuse to the sufficient degree for permanently holding and occluding the opening, terminating the application of energy in a time-delayed relationship to the detection of the precursor fusion condition which permits the sufficient degree of energy to be conducted to the compressed apposed sidewall portions; and thereafter cooling the apposed sidewall portions while the sidewall portions are compressed to permit the fibers of the compressed apposed sidewall portions to intertwine and fuse with one another to the sufficient degree to hold the apposed sidewall portions permanently together and occlude the opening permanently.

Another aspect of the invention involves a tissue sealing apparatus for coaptively sealing a sidewall of biological tissue which surrounds and defines an opening in the tissue to occlude the opening. The tissue sealing apparatus comprises a handpiece having jaws movable to close on and compress portions of the sidewall in apposition to one another to occlude the opening, and an electrical energy generator connected to the handpiece to deliver electrical energy to the jaws. The generator delivers sufficient energy for conduction from the jaws through the compressed apposed sidewall portions to cause the fibers of the compressed apposed sidewall portions to intertwine and fuse with one another to a sufficient degree to hold the apposed sidewall portions together permanently and to occlude the opening permanently. The tissue sealing apparatus also includes a controller connected to the generator and the handpiece. The controller includes a switch which is movable between opened and closed positions in response to a control signal supplied to the switch. In the closed position the switch conducts the energy from the generator through the controller to the jaws of the handpiece, and in the opened position the switch terminates the conduction of energy from the generator to the handpiece. The controller also includes a detector which senses a characteristic of the energy conducted from the generator to the handpiece. The detector determines a precursor fusion condition from the sensed characteristic of the energy before sufficient energy has been applied from the jaws to the sidewall to cause the fibers to intertwine and fuse to a sufficient degree to hold the apposed sidewall portions together permanently and to occlude the opening permanently. The detector delivers a trigger signal upon detecting the occurrence of the precursor fusion condition. The controller includes an energy completion device connected to the detector and to the switch. The energy completion device asserts a termination signal as a control signal to the switch to cause the switch to change from the closed position to the opened position at a subsequent time relative to the assertion of the trigger signal and when sufficient energy has been applied to the compressed apposed sidewall portions to cause the fibers of the compressed apposed sidewall portions to intertwine and fuse with one another to a sufficient degree to hold the apposed sidewall portions permanently together and occlude the opening permanently.

A further aspect of the invention involves using a controller of the general nature described to connect a conventional electrosurgical generator to a conventional tissue sealing handpiece to create a tissue sealing apparatus.

These aspects of the invention may be supplemented by further preferable improvements and features involving some or all of the following: terminating the application of energy relative to the detection of the precursor fusion condition at a fixed time duration after the detection of the precursor fusion condition; detecting the precursor condition solely from a characteristic of RF current conducted within a predetermined time through the compressed apposed portions of the sidewall; detecting the precursor fusion condition by comparing values of the RF current to a predetermined threshold value, and doing so during a predetermined threshold time, and doing so when peak values of the RF current do not exceed the threshold value during the threshold time; and terminating the application of energy at a predetermined energy completion time after the precursor fusion condition has been detected. In a preferred form, the threshold time may range between 100 to 200 milliseconds, with an optimum of approximately 150 milliseconds, while the energy completion time is approximately 980 milliseconds.

A more complete appreciation of the scope of the present invention and the manner in which it achieves the above-noted and other improvements can be obtained by reference to the following detailed description of presently preferred embodiments taken in connection with the accompanying drawings, which are briefly summarized below, and by reference to the appended claims.

BRIEF DESCRIPTION OF THE DRAWINGS

FIGS. 8 and 9 are waveform diagrams having a common time reference which illustrate certain signals present in the controller shown in FIG. 7.

FIGS. 10 and 11 are waveform diagrams having a common time reference which illustrate certain signals present in the controller shown in FIG. 7.

FIGS. 12, 13 and 14 are waveform diagrams having the same common time reference as that of FIGS. 8 and 9, which illustrate certain signals present in the controller shown in FIG. 7.

DETAILED DESCRIPTION

Figure 1:
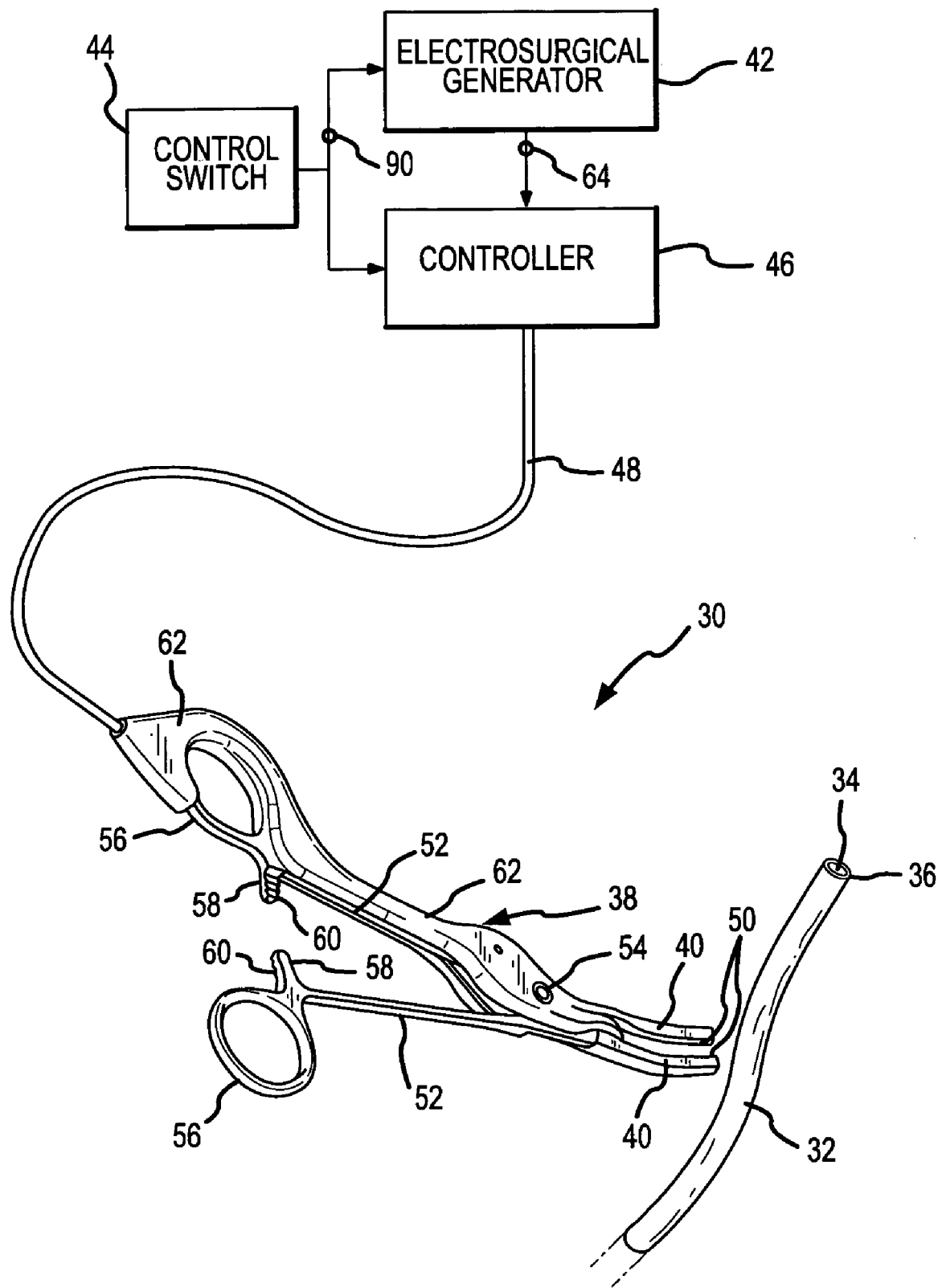
FIG. 1 is an illustration of a coaptive biological tissue sealing apparatus embodying the present invention, along with a portion of a biological vessel on which a tissue sealing treatment cycle is performed.
Figure 2:
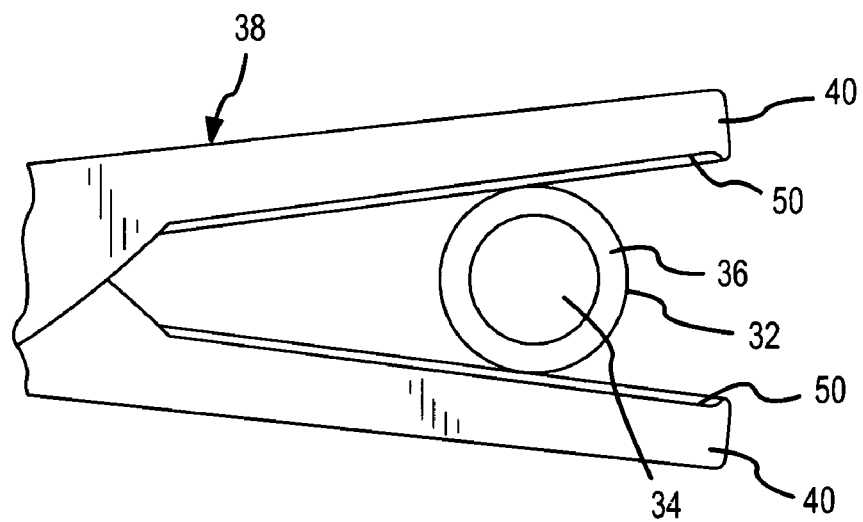
FIG. 2 is an enlarged partial side elevational view of jaws of a handpiece of the apparatus shown in FIG. 1, illustrating the jaws on either side of a vessel shown in cross-section before commencing the tissue sealing treatment cycle.

A coaptive biological tissue sealing apparatus 30, the use of which also exemplifies the practice of a method of coaptively sealing biological tissue, both of which incorporate the present invention, is shown in FIG. 1. The coaptive tissue sealing apparatus 30 is used to permanently close a lumen, duct, passageway or chamber formed in and surrounded by the biological tissue. The biological tissue is exemplified in FIG. 1 (and FIGS. 2-4) by a biological vessel 32, such as an artery or vein. Other examples of biological tissue which may be permanently sealed by use of the present invention include fallopian tubes, bile ducts, tissue surrounding an aveoli or air sac in the lung, the colon or bowel, and any other structure where ligation might otherwise be performed.

For the present purposes of describing preferred embodiments of the sealing apparatus 30 and the coaptive sealing method which incorporate the present invention, the vessel 32 will be used as an example of the biological tissue which is sealed, and a lumen 34 in the vessel 32 will exemplify the lumen, duct, passageway or chamber which is to be permanently occluded by sealing the biological tissue. The biological tissue of the vessel 32 is represented by a sidewall 36 of the vessel 32. The lumen, duct, passageway or chamber in the biological tissue will be referred to generically as an "opening" in the context of the following appended claims which define the invention, although this detailed description of the preferred embodiments may also occasionally refer to an "opening" in the same generic context. That portion of the biological tissue which surrounds and defines the "opening" will be referred to as a "sidewall" in the context of the following appended claims which define the invention, and throughout this detailed description of the preferred embodiments since the vessel 32 is defined by its sidewall 36. Therefore, in accordance with this naming convention, the sidewall 36 of the vessel 32 as used in the following detailed description is one example of "sidewall" of the biological tissue which is sealed, and the lumen 34 of the vessel 32 is one example of an "opening" which may be permanently occluded or closed by sealing the apposite portion of the "sidewall" of the biological tissue which initially defined and surrounded the "opening".

A conventional hand piece 38 of the apparatus 30 is manipulated by a surgeon or medical personnel to grip the vessel 32 or other tissue between jaws 40 of the handpiece 38 and compress opposite portions of the sidewall 36 of the vessel 32 in apposition with one another to occlude a lumen 34 through the vessel 32 and to force the apposed sidewall portions 36 into a diminished thickness compared to their natural thickness. Thereafter a conventional electrosurgical generator (ESG) 42 is activated to deliver electrosurgical energy to the compressed apposite portions of the vessel sidewall 36. The electrosurgical energy delivered by the electrosurgical generator 42 in accordance with the present invention is typically bipolar radio frequency (RF) electrosurgical energy. The energy is delivered from the electrosurgical generator 42 in response to closing or otherwise activating a control switch 44, such as a conventional ESG foot switch. The electrosurgical energy is conducted through a controller 46 and through a cable 48 to the jaws 40 of the handpiece 38. The jaws 40 include electrodes 50 for conducting the electrosurgical energy through the compressed apposite portions of the sidewall 36 of the vessel 32.

The electrical energy is conducted through the compressed apposite portions of the vessel sidewall 36 and heats those sidewall portions. The compressed apposite sidewall portions are permanently fused or sealed together as a result of the mechanical compression force and the heat created by electrical energy conducted through the sidewall portions. The fusion of the apposite sidewall portions permanently occludes the lumen 34 through the vessel 32, thereby preventing fluid which is normally conducted through the lumen 34 from leaking through the occlusion and from the vessel 32.

Reliably and permanently occluding the vessel 32 is very important in surgery. In the case of the vessel 32 being an artery or a vein, the permanent occlusion prevents blood loss during the surgical procedure and after the procedure has been completed and any incision in the patient has been closed. In the case of lung tissue, sealing the aveoli permits the lung to function as an air-tight enclosure which is necessary for effective respiration. The integrity of the occlusion is sufficient to withstand the normal range of pressures of the fluid within the biological tissue. In the case of an artery or a vein, that normal range of pressures will be the systolic and diastolic blood pressure. Typically, the seal created by the present invention will have sufficient integrity to withstand ruptures from a range of fluid pressures which is considerably greater than the normal range of pressures experienced by the biological tissue which defines the lumen or opening within the vessel.

The technique for fusing or sealing biological tissue is relatively well-known. The application of the heat energy combined with sufficient compression of the apposed sidewall portions of the vessel 32 first loosens or denatures the natural intertwined or cross-linked fibers within the tissue, principally collagen and elastin fibers. Loosening the natural physical structure of these fibers makes them more malleable or flexible and allows them to fuse and reform into another different intertwined physical structure with other fibers while cooling. The compression of the tissue while the fibers are loosened and flexible allows the fibers of the apposed sidewall portions to intertwine with one another, thereby permanently creating a fused intertwined physical structure of those fibers, and this fused intertwined physical structure permanently seals the apposed sidewall portions together into the permanent occlusion of the lumen 34 or opening.

A number of factors can influence the strength and integrity of the occlusion. If the compression of the sidewall portions is insufficient, the fibers will not be sufficiently close or proximal to one another to create enough intertwining and fusion to hold the tissue portions together. In general, the necessity to apply sufficient compression to the sidewalls of the tissues has been recognized as a necessity to achieve adequate sealing or fusion of the biological tissue. Compressing the sidewall 36 is accomplished by use of the handpiece 38.

Figure 3:
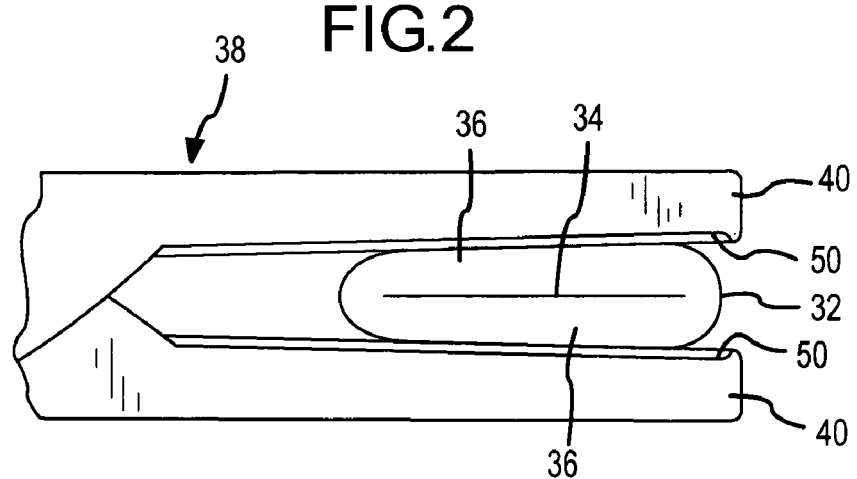
FIG. 3 is a side elevational view of the jaws shown in FIG. 2, illustrating compressing the vessel during the tissue sealing treatment cycle.

Although the handpiece 38 may assume different forms, the type of handpiece 38 shown in FIG. 1 includes two arms 52 which are pivotally connected together at a middle pivot point 54 to locate the jaws 40 on the distal ends of the arms 52. Finger enclosures 56 are formed on the opposite end of the arms 52 from the jaws 40. Squeezing finger enclosures 56 toward one another pivots the arms 52 about the pivot point 54 and moves the jaws 40 toward one another from an open position surrounding the vessel 32, shown in FIG. 2. Further movement of the finger enclosures 56 toward one another causes the jaws 40 to compress the sidewall 36 and close the lumen 34, as shown in FIG. 3. In the state shown in FIG. 3, the opposite portions of the sidewall 36 have contacted one another in apposition and completely close the lumen 34. The relative thickness of the apposite portions of the sidewall 36 has compressed somewhat to the limit of the force applied from the jaws 40 against the unheated sidewalls 36 of the vessel 32.

The resistance of compressing the apposite portions of the sidewall 36 causes the arms 52 to deflect toward one another along their longitudinal extension. Tabs 58 extend toward one another near the proximal end of the arms 52 on the opposite side of the arms 52 from the finger enclosures 56 (FIG. 1). The tabs 58 include teeth 60 which extend from the tabs 48 in a mutually facing relationship. The teeth 60 selectively engage one another and disengage from one another when the proximal ends of the arms 32 move close to one another as a result of finger pressure applied by squeezing the finger enclosures 56. The teeth 60 engage one another in a ratchet-like or detent-like manner to maintain the compressive force on the apposite portions of the sidewall 36. In this manner, the user is not required to maintain the compressive force on the apposite sidewall portions. The teeth 60 of the tabs 58 remain engaged with one another while the sidewall 36 of the vessel 32 is heated. The electrical energy is applied to the compressed apposite sidewalls 36 as shown in FIG. 3.

As the compressed apposite sidewall portions are heated, the tissue structure of the sidewall 36 collapses to reduce the resistance created by compression of the tissue between the jaws 40. The jaws 40 move slightly closer to one another as a result of the tissue collapse. Some of the resistance force caused by the initial compression of the tissue between the jaws 40 is diminished, causing the amount of deflection of the arms 52 to be slightly reduced. However, the amount of resistance resulting from tissue collapse is not so great as to completely eliminate any resistance from the heated and compressed apposite portions of the sidewall 36, and therefore the resistance still maintains the teeth 60 of the tabs 58 of the handpiece engaged together. The continued engagement ensures that pressure is continuously applied to the apposite compressed portions of the sidewall 36 until the handpiece 38 is removed from the sealed vessel 32. To remove the handpiece 38, the teeth 60 of the tabs 58 are disengaged from one another by deflecting the arms 52 to separate the tabs 58 from one another, thereby releasing the vessel 32 from the jaws 40.

The electrodes 50 are positioned on the jaws 40 and are electrically insulated from the jaws to conduct the electrical energy between one another and through the apposite compressed portions of the sidewall 36. In one type of handpiece 38, the electrodes 50 are part of a disposable assembly which is connected to at least one of the arms 52 and to both jaws 40. The electrodes 50 conduct the bipolar electrical energy as a result of connecting the electrode 50 on one jaw 40 to one pole of the bipolar electrical energy and connecting the electrode 50 on the other jaw 40 to conduct the other pole of the bipolar electrical energy. The two poles of bipolar electrical energy are conducted through separate conductors within the cable 48 and through an enclosure 62, which is attached to one of the arms 52 and which is part of the disposable assembly, to the electrodes 50 on the jaws 40.

Figure 4:
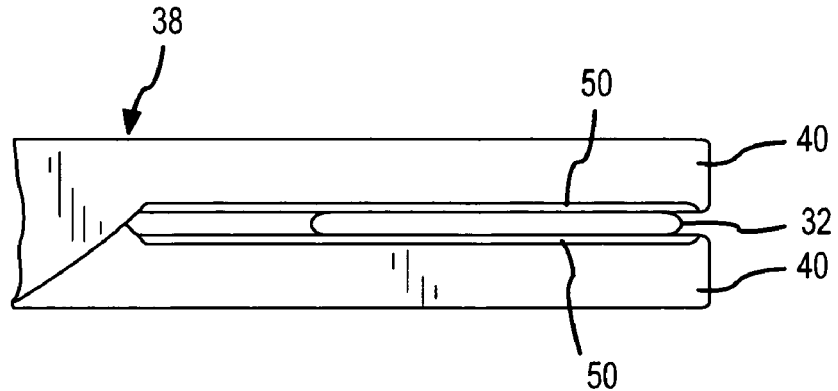
FIG. 4 is a side elevational view of the jaws shown in FIGS. 2 and 3, illustrating complete closure of the jaws on the vessel during the tissue sealing treatment cycle.

Since the electrodes 50 are connected to electrically opposite poles of the output energy from the electrosurgical generator 42, it is important that the electrodes 50 are not allowed to contact one another. Such contact would result in short-circuiting the bipolar electrosurgical energy delivered from the electrosurgical generator 42 and might damage the generator 42. To prevent the electrodes 50 from contacting one another, the mechanical structure of the handpiece 38 prevents the jaws 40 from completely closing in contact with one another as the tissue is heated as shown in FIG. 4. Instead, the jaws 40 stop moving toward one another at a position which creates a relatively narrow and uniform width gap of about 0.1 mm between the jaws 40. Fixing the gap between the jaws 40 in this manner also prevents the jaws 40 from mechanically severing the vessel 32 as a result of energy or pressure applied during tissue fusion.

The parallel facing relationship of the jaws 40 also creates a relatively uniform thickness of apposite compressed portions of the sidewall 36 between the electrodes 50. The uniform thickness of the apposite compressed sidewall portions provides a relatively uniform and equally distributed electrical load for conducting the electrical energy uniformly between electrodes 40 and through the compressed apposite sidewall portions of the vessel 32. The relatively uniform load distributes the electrical energy uniformly across the lateral dimension of the apposite compressed sidewall portions, thereby assuring that the amount of heating is approximately uniform in the lateral sense across the compressed apposite sidewall portions. Uniform distribution of the electrical energy is important to prevent some locations of the compressed apposite sidewall portions from becoming too hot and permanently influencing adversely the ability of the tissue fibers to fuse and intertwine while leaving other locations of the compressed apposite sidewall portions without enough heat to adequately fuse and intertwine the fibers in those locations. The uniform energy distribution assures that all locations along the lateral width of the compressed apposite sidewall portions are heated approximately to the same extent at approximately the same time to achieve effective tissue fusion.

Another factor which can influence the strength and integrity of the tissue fusion is the amount and characteristics of the energy applied to heat and otherwise influence the fusing and intertwining characteristics of the fibers in the tissue. The application of the energy for heating the tissue is particularly important because it is more difficult to control compared to the compression of the tissue. Compression of the tissue, as described in conjunction with FIGS. 3 and 4, is relatively consistently obtained due to the mechanical nature of the handpiece and its ability to compress the apposite sidewall portions to approximately the same extent. If insufficient heat is applied, the fibers will not loosen sufficiently to reform in a fused and intertwined matter. If excessive heat is applied, the fibers are adversely affected to the point that they do not fuse and intertwine in the best effective manner. When RF electrosurgical energy is used for tissue fusion, applying the additional energy necessary to achieve adequate tissue fusion will generally result in the generation of arcs of the RF energy. The arcs have the tendency to penetrate into the tissue and may weaken the sidewall adjacent to the fused apposite sidewall portions, thereby diminishing the strength of the sidewall and creating the possibility of fluid leaks at the sealed location or at locations adjacent to the sealed location. It is therefore important to control the amount of energy applied to the tissue to achieve the best seal to avoid the problems associated with inadequate and excessive energy and heat application.

The controller 46 controls the amount of energy applied to the tissue to obtain the best seal from fusing and intertwining the tissue fibers. The functionality of the controller 46 is based on the recent discovery that the energy application for tissue sealing is controlled very advantageously in relation to a precursor fusion condition involving the peak RF current delivered to the tissue not exceeding a predetermined threshold for a predetermined threshold time, as is described in greater detail below. After the occurrence of this precursor fusion condition, it is necessary to deliver additional energy to the tissue to obtain an effective seal or fusion of the compressed apposite sidewall portions of the tissue. Terminating the delivery of electrosurgical energy at the moment when the precursor fusion condition exists has been shown experimentally not to result in an effective seal. In other words, terminating the application of heating energy when the precursor fusion condition occurs results in an insufficient number of collagen and elastin issue fibers having loosened adequately enough to intertwine and fuse with one another. The additional energy is believed to be necessary to obtain the loosening, fusing and intertwining of the relatively high denaturing temperature collagen and elastin fibers within the tissue.

The additional energy added after the occurrence of the precursor fusion condition must be sufficient to drive off a substantial portion of the intracellular fluid within the cells of the tissue. Removing the intercellular fluid is believed to create the beneficial effect of locating tissue fibers within sufficiently close physical proximity to fuse and intertwine without the intracellular fluid interfering with the fusion and intertwining. Eliminating a substantial portion of the intracellular fluid is accomplished by delivering enough additional energy to vaporize the intracellular fluid. Typically the intracellular fluid is predominantly water. Consequently, the temperature of the intracellular fluid must be raised to or above 1000 Celsius in order to vaporize that intercellular fluid.

The controller 46 monitors an RF current 64 (FIG. 5) delivered from the electrosurgical generator 42 to determine the existence of the precursor fusion condition. The controller then permits the continued delivery of the additional electrical energy for a predetermined time sufficient to achieve effective tissue fusion before terminating delivery of electrical energy to the tissue. When the delivery of electrosurgical energy is terminated, the heated and compressed apposite sidewall portions are allowed to cool, to complete the fusion of the tissue. Thereafter the handpiece 38 is removed from the vessel 32. If desired, the vessel 32 can then be severed at a location adjacent to the fused apposed sidewall portions. In some circumstances, two seals at fusion locations which are longitudinally displaced along the vessel 32 may be created, so that the vessel can be severed between those seals or fusion locations.

Figure 5:
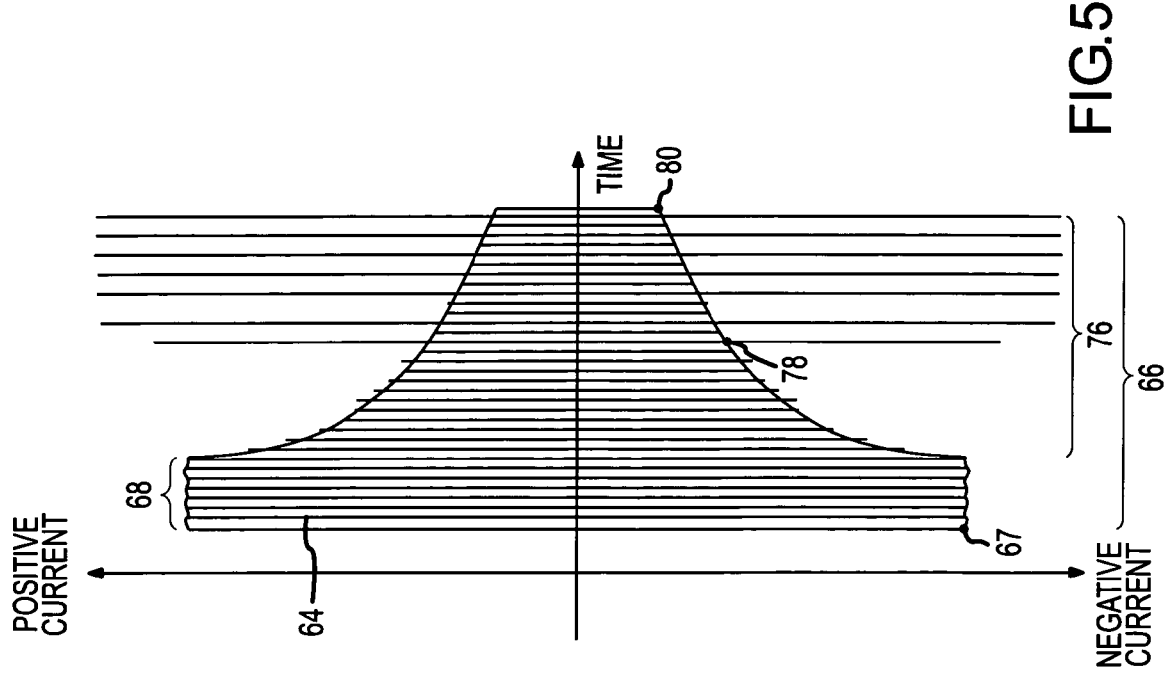
FIG. 5 is a waveform diagram of current applied to the tissue by the tissue sealing apparatus shown in FIG. 1 during an exemplary tissue sealing treatment cycle.

The condition of the RF current 64 which is monitored by the controller 46 is understood by reference to FIG. 5, which shows the RF current 64 delivered from the electrosurgical generator 42 and conducted through the compressed apposite portions of the sidewall 36 (FIGS. 3 and 4) during a single treatment cycle 66 in which tissue fusion or sealing is achieved. The treatment cycle 66 begins with an initial delivery of the RF current 64 from the electrosurgical generator 42 at cycle starting point 67 during an initial heating phase 68 of the treatment cycle 66. During the initial heating phase 68, the peak RF current 64 delivered to the compressed apposite sidewall portions is relatively constant. The peak value and amount of the RF current 64 delivered during the initial heating phase 68 is dependent primarily on the capability of the electrosurgical generator to deliver power into relatively low resistance or impedance tissue. The RF current 64 begins to heat the compressed apposite portions of the sidewall 36 of the vessel 32. The temperature of the compressed apposite sidewall portions increases and is generally related to the amount of energy delivered to the tissue during the initial heating phase 68, and generally increases substantially linearly during the initial heating phase 68.

After the initial heating phase 68, the envelope of the non-arcing RF current 64 decreases during a current reduction phase 76 of the treatment cycle 66, primarily as a result of desiccation of the tissue resulting from vaporization of the intracellular fluid. As the desiccation continues, the impedance of the tissue increases to a point where arcing may commence, at point 78. The arcs are illustrated by the relatively high-amplitude and short time duration spikes in the RF current 64, in both the positive and negative directions. Although the arcing which commences at point 78 causes microscopic tissue destruction and weakening due to the arcs penetrating into the tissue which raises the potential for compromising the integrity of the sealed tissue, it is nevertheless necessary to apply the additional energy to the compressed apposite sidewall portions to create an adequate seal. An important aspect of the present invention is that only that amount of additional energy necessary for a good seal is applied, and as a result, the amount of arcing which occurs is limited to the amount necessary to obtain the good seal. Thereafter at the termination of the treatment cycle 66 at point 80, the controller 46 terminates the delivery of electrical energy to the tissue.

Figure 6:
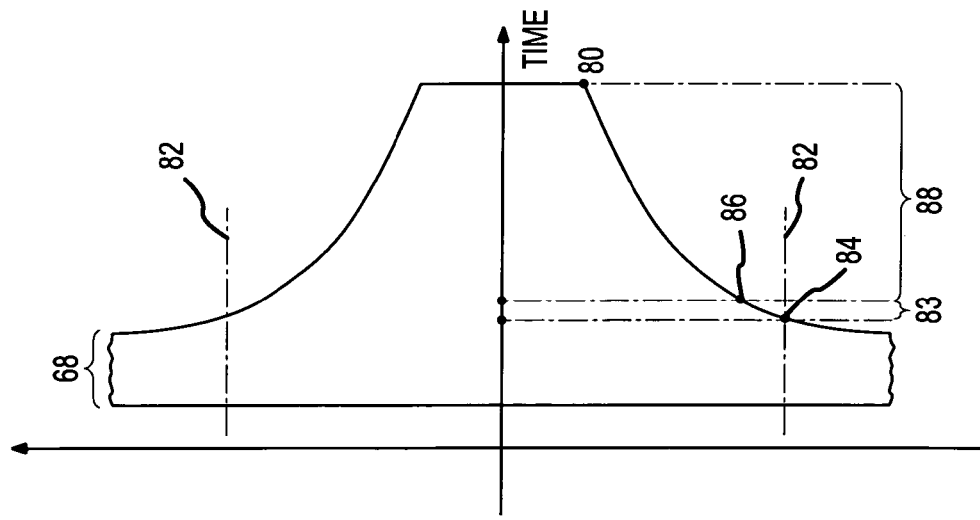
FIG. 6 is diagram of an envelope of the non-arcing portion of the current waveform shown in FIG. 5, showing various points during the tissue sealing treatment cycle.

The precursor fusion condition is typically determined during the current reduction phase 76 of the treatment cycle 66. However, in some circumstances, the precursor fusion condition may be determined during the initial heating phase 68. To determine the precursor fusion condition, a detector of the controller 46 establishes a threshold value 82, which as shown in FIG. 6 is somewhat lower than the peak RF current occurring during the initial heating phase 68. After the peak RF current 64 initially falls below the threshold value 82 at point 84, the controller 46 thereafter determines that the peak RF current 64 remains below the threshold value 82 for a predetermined threshold time 83 commencing after point 84. The threshold time 83 ends at point 86. Therefore, the relative time between points 84 and 86 defines the threshold time 83 during which the peak RF current 64 must remain below the threshold value 82. The duration of the threshold time 83 during which the peak RF current 64 must remain below the threshold value 82 happens so that the point 86 occurs before the arcing commences at point 78 (FIG. 5). Accordingly, the arcing will not interfere with the determination of the precursor fusion condition established by the peak RF current value not exceeding the threshold value 82 during the threshold time 83 between points 84 and 86.

If the peak RF current 64 exceeds the threshold value 82 at any time during the threshold time 83, the measurement of the precursor fusion condition is commenced again beginning immediately after the peak RF current exceeded the threshold value. On the other hand, if the peak RF current 64 exceeds the threshold value 82 after of the threshold time 83 has been established, that condition is ignored. However, the possibility of the peak RF current exceeding the threshold value after the threshold time has been established is relatively remote.

After it has been determined that precursor fusion condition has occurred as a result of the peak RF current not exceeding the threshold value 82 for the duration of the threshold time 83 between points 84 and 86, an energy completion time or delivery window 88 is established by the controller 46. The energy completion time 88 commences at point 86 and extends to point 80, where the treatment cycle 66 ends as a result of the controller 46 terminating the delivery of energy from electrosurgical generator 42 to the tissue. Thus, during the energy completion time 88 or delivery window between points 86 and 80, the additional amount of energy is delivered from the electrosurgical generator to the tissue necessary to assure effective tissue fusion.

Figure 7:
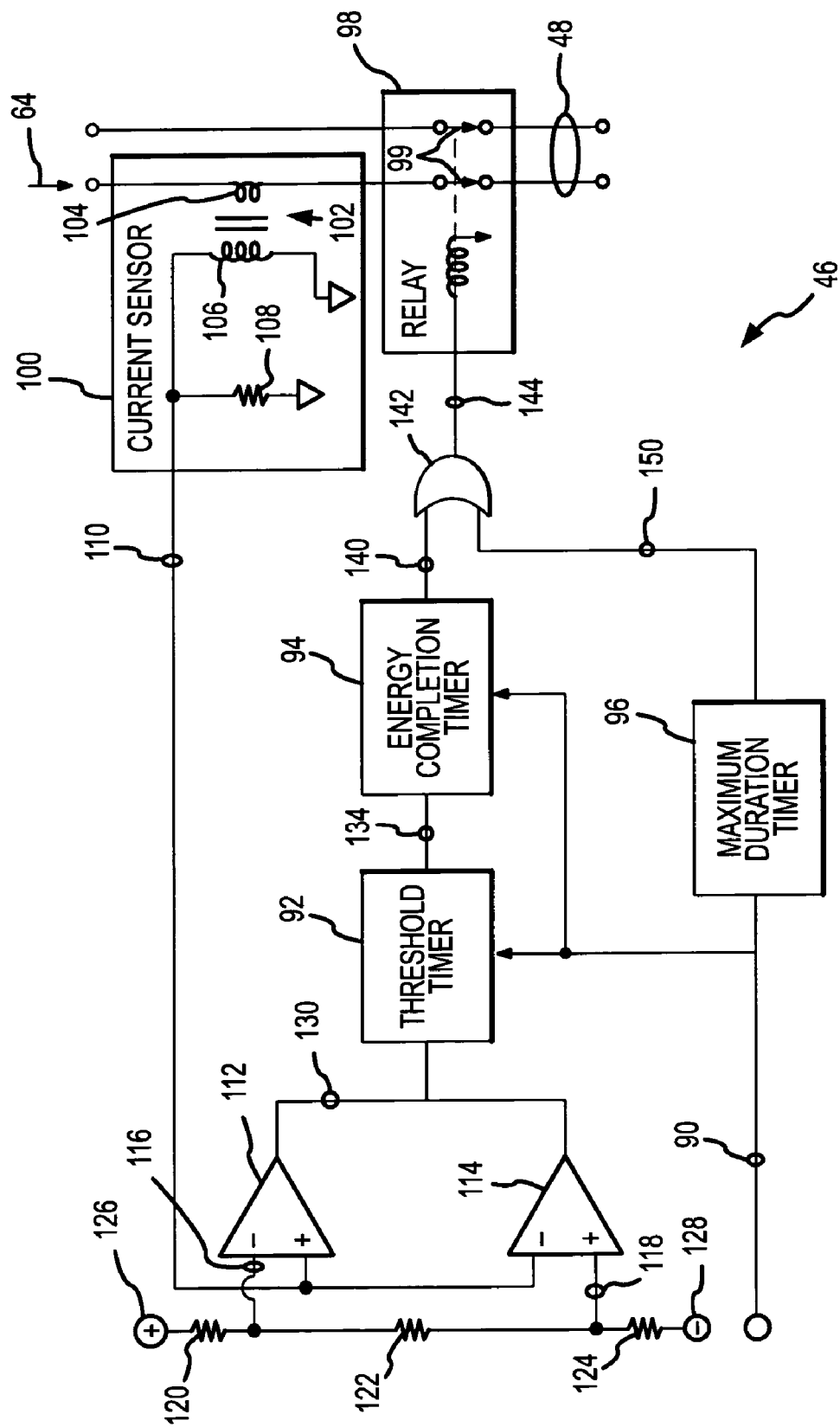
FIG. 7 is a circuit diagram of electronic components of a controller of the tissue sealing apparatus shown in FIG. 1.

The functional components of the controller 46 which achieve the RF current monitoring and controlling functions are shown and described in conjunction with FIG. 7 taken in conjunction with FIGS. 5, 6 and 8-14 which illustrate waveforms of various signals applicable to the components of the controller shown in FIG. 7.

The treatment cycle 66 begins when the control switch 44 is closed or activated (FIG. 1). Activation of the control switch 44 delivers an activation signal 90 (FIG. 8) to the electrosurgical generator 42 and the controller 46 (FIG. 1). The activation signal 90 causes the electrosurgical generator 42 to begin delivering output electrosurgical energy of which the RF current 64 is a constituent part. In the controller 46, the activation signal 90 enables a threshold timer 92, an energy completion timer 94, and a maximum treatment duration timer 96. The threshold timer 92 and the maximum treatment duration timer 96 commence counting time values which have been established for those timers 92 and 96 in response to the activation signal 90. The energy completion timer 94 requires the application of a precursor trigger signal 134 to commence timing. A relay 98 includes switch contacts 99 which are normally closed. The normally closed switch contacts 99 conduct the electrosurgical RF current 64 from the electrosurgical generator 42 through the controller 46 to the cable 48 and the handpiece 38 (FIG. 1).

The characteristics of the RF current 64 conducted through the controller 64 are sensed by a current sensor 100. The current sensor 100 includes a current sense transformer 102 having a primary winding 104 through which the RF current 64 flows. A secondary winding 106 of the current sense transformer 102 develops a secondary current which is directly related to the magnitude and characteristics of the RF current 64. The secondary current from the secondary winding 106 is conducted through a resistor 108, and a voltage is developed across the resistor 108 which is directly related to the characteristics of the RF current 64 delivered by the electrosurgical generator 42. The voltage developed across the resistor 108 is a current sense signal 110.

Comparators 112 and 114 receive the sense signal 110 and two threshold comparison signals 116 and 118. The threshold comparison signals 116 and 118 are developed by a voltage divider formed by resistors 120, 122 and 124 which are connected in series between a positive power supply 126 and a negative power supply 128. The magnitudes of the threshold comparison signals 116 and 118 correspond to the positive and negative values of the threshold value 82 (FIG. 6). Positive and negative threshold comparison signals 116 and 118, respectively, are required to assure that the peak RF current 64 does not exceed the threshold value 82 (FIG. 6) in either the positive or the negative sense, since the RF current 64 alternates in positive and negative half cycles. The values of the resistors 120, 122 and 124 establish the level of the threshold comparison signals 116 and 118 as equal to one another but of opposite polarity with respect to reference potential.

The threshold comparison signal 116 is applied to the inverting input terminal of the comparator 112. The threshold comparison signal 118 is applied to the noninverting terminal of the comparator 114. The sense signal 110 is applied to the noninverting input terminal of the comparator 112 and to the inverting input terminal of the comparator 114. The comparators 112 and 114 determine if the peak amplitude of the sense signal 110 is greater or less than the threshold comparison signals 116 and 118. As understood from FIGS. 10 and 11, during those times when the sense signal 110 exceeds the upper threshold comparison signal 116, and during those times when the sense signal 110 is less than the lower threshold comparison signal 118, one of the comparators 112 and 114 asserts a reset signal 130 at a logic high level. During those times when the sense signal 110 is less than the upper threshold comparison signal 116 and is less negative than the lower threshold comparison signal 118, the comparators 112 and 114 assert the reset signal 130 at a logic low level. Should the sense signal 110 exceed only the positive threshold comparison signal 116 but not be more negative than the negative threshold comparison signal 118, or alternatively should the sense signal 110 be more negative than the negative threshold comparison signal 118 but not exceed the positive threshold comparison signal 116, the applicable one of the comparators 112 or 114 will assert the reset signal 130 at the logic high level. In this manner, should either of the threshold comparison signals 116 or 118 be exceeded in either the positive or the negative sense by the positive and negative half cycles of the sense signal 110, a high-level reset signal 130 will be asserted to the threshold timer 92.

The threshold timer 92 is enabled to commence counting in response to the assertion of the activation signal 90. Because the RF current 64 is relatively high during the initial heating phase 68 compared to the threshold value 82 (FIG. 6), the peak values of the sense signal 110 will exceed the positive and negative threshold comparison signals 116 and 118 almost immediately after the RF current 64 is initially delivered from the electrosurgical generator 42. The comparators 112 and 114 assert the reset signal 130 as the positive and negative half cycles of the sense signal 110 exceed the threshold comparison signals 116 and 118 in a positive and negative sense. Consequently, the threshold timer 92 is repeatedly reset by the assertion of the reset signal 130 to prevent it from counting down to the full duration of the threshold time 83 (FIG. 12). It is only when the reset signal 130 remains at a logic low level for a sufficient time to allow the threshold timer 92 to complete its count of the threshold time 83 that the threshold timer 92 is able to assert the precursor trigger signal 134 (FIG. 13). The assertion of the precursor trigger signal 134 indicates that the threshold timer 92 has successfully counted down to zero. The successful count down to zero begins after the last time that the reset signal 130 changes from a logic high level to a logic low level, as shown at 131 in FIGS. 12 and 13. While the threshold timer 92 is counting but has not reached the final count of the threshold time 83, the precursor trigger signal 134 is asserted at a logic low level. The transition between the logic low level and the logic high level of the precursor trigger signal 134 occurs at 138 shown in FIG. 13. When the threshold timer 92 counts down to zero, thereby indicating the expiration of the threshold time 83, the assertion of the logic high precursor trigger signal 134 indicates that the RF current 44 has remained below the threshold value 82 (FIG. 6) for the threshold time 83.

The energy completion timer 94 responds to the assertion of a high-level precursor trigger signal 134 by commencing to count the energy completion time 88 as indicated at 138 in FIG. 14. Once the energy completion timer 94 has counted down to zero, the energy completion timer 94 changes a termination signal 140 from a logic low level to a logic high level as shown at 141 in FIG. 14. An OR gate 142 is connected to receive the termination signal 140 from the energy completion timer 94. When the termination signal 140 changes from a low level to a high level, the OR gate 142 delivers a relay control signal 144 at 141 to the relay 98 as shown in FIG. 9.

The relay 98, which has switch contacts 99 that are normally closed, responds to the relay control signal 144 by opening the switch contacts 99 and thereby terminating the flow of the RF current 64 from the generator 42 to the handpiece 38. Opening the switch contacts 99 discontinues the delivery of electrical energy to the vessel 32 at the energy delivery termination point 80 (FIG. 6).

The maximum duration timer 96 assures that the electrical energy from the generator 42 is not applied to the tissue of the vessel 32 for an excessively long amount of time. The maximum duration timer 96 receives the activation signal 90 from the control switch 44 (FIG. 1) at the same time that the electrosurgical generator 42 begins delivering electrosurgical energy to the handpiece 38. The activation signal 90 enables the maximum duration timer 96 to start counting down a maximum duration time for the entire treatment cycle 66. The maximum duration timer 96 is preferably set with a maximum duration time of approximately 18 seconds. If the maximum duration timer 96 counts all the way down to zero after 18 seconds, the timer 96 asserts a maximum duration signal 150 to the OR gate 142. The OR gate 142 responds by asserting the relay control signal 144 to the relay 98 which causes the switch contacts 99 to open and terminate the delivery of electrical power to the handpiece 38.

The maximum duration timer 96 is set to a time that is longer than the duration of a normal treatment cycle 66 (FIG. 5) is expected to last under normal conditions. If the maximum duration timer 96 terminates the power delivery, then an unexpected problem or condition exists. That unexpected problem may be safety related and terminating the delivery of further electrosurgical energy under these conditions may be warranted, at least for the particular treatment cycle 66 which has then been attempted.

Figure 15:
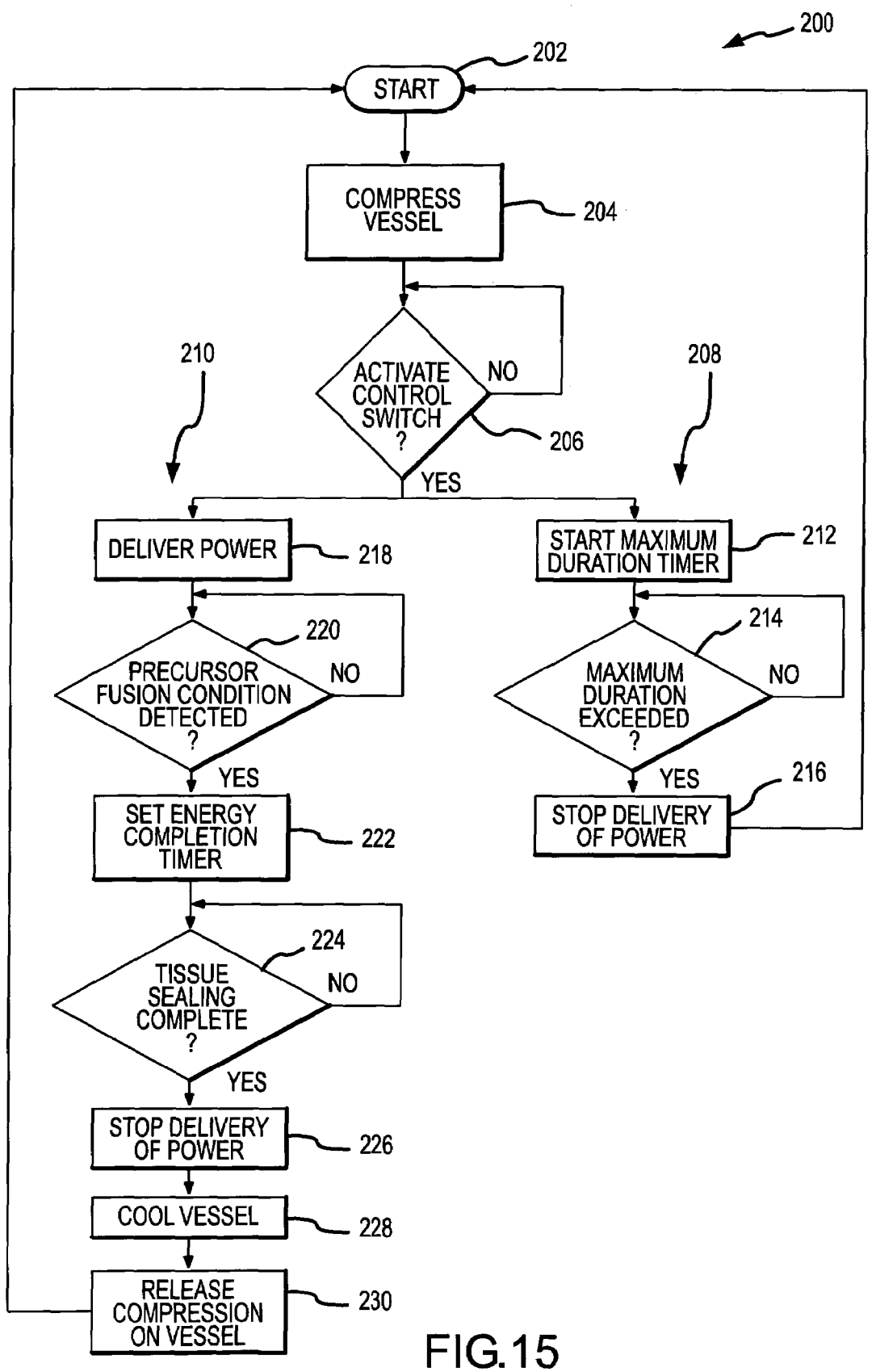
FIG. 15 is a flowchart illustrating aspects of a process flow executed by the tissue sealing apparatus in FIG. 1 when performing the tissue sealing treatment cycle, and also illustrating method aspects of the present invention.

The events involved in operating and using the coaptive sealing apparatus 30 during a treatment cycle 66, and the events involved in performing the method of coaptive tissue sealing, are summarized in the sequence 200 shown in FIG. 15. The sequence 200 begins at 202. Thereafter, the vessel 32 is compressed at 204 (FIG. 4), by use of the handpiece 38 (FIG. 1). Next, it is determined at 206 whether the control switch 34 (FIG. 1) has been activated. If the determination at 206 is negative, then a waiting loop is executed until the control switch 34 is activated. Activation of the control switch is recognized by a positive determination at 206. At this point, the sequence 200 diverges into two simultaneously-executed sub-series of events 208 and 210. The sub-series of events 208 involve limiting the maximum time duration of the treatment cycle 66, and the sub-series of events 210 involve the normal execution of a treatment cycle 66 for fusing or sealing tissue.

The sub-series of events 208 commences at 212 with starting the maximum duration timer 96 (FIG. 7) to begin its countdown. Next, a determination is made at 214 as to whether the maximum time duration established by the timer 96 has been reached. A waiting loop is executed as indicated by the negative determination at 214 until the maximum time duration established by the timer 96 has been reached or counted down to zero. If the maximum time duration is reached, as indicated by an affirmative determination at 214, the delivery of electrical energy is terminated at 216, as a result of opening the switch contacts 99 of the relay 98 (FIG. 7). As discussed previously, a normal treatment cycle 66 is typically completed well before the maximum duration timer 96 terminates the delivery of electrical energy from the generator to the handpiece. The sub-series of events 208 come into play only under conditions when the normal functionality of the treatment cycle 66 fails for some unexpected reason. Normally speaking the normal treatment cycle 66 represented by the sub-series of events 210 will be executed as intended, and consequently, the sub-series of events 208 will not be completed as just described.

The sub-series of events 210 relate to the execution of a normal treatment cycle 66. The execution of a normal treatment cycle commences with the delivery of electrosurgical energy at 218. After the energy delivery begins, a determination is made at 220. The determination made at 220 involves detecting whether the precursor fusion described above has occurred. If the precursor fusion condition has not been detected, the determination at 220 is negative and a waiting loop is executed until the precursor fusion condition has been detected by a positive determination at 220.

A positive determination at 220 triggers the energy completion timer 94 (FIG. 7) at 222 to begin counting the energy completion time 88 (FIGS. 5, 6 and 14). Next, a determination is made at 224 as to whether the tissue sealing is complete as represented by the energy completion timer 94 (FIG. 7) counting down to zero. Until the tissue sealing is complete and the energy completion timer has counted down to zero, a waiting loop is executed. When the determination at 224 is affirmative, indicating that the electrosurgical generator 42 has applied an adequate amount of electrical energy to the tissue for an effective seal, the sequence advances to 226, where the delivery of the electrosurgical energy is terminated. Under these circumstances, the switch contacts 99 of the relay 98 (FIG. 7) are opened, and the delivery of energy from the electrosurgical generator 42 is terminated, despite the fact that the control switch 44 (FIG. 1) may remain activated or closed.

After terminating the power delivery 226, the opposed portions of the sidewall 36 of the tissue (FIGS. 3 and 4) are allowed to cool at 228 while the compressive force or pressure remains applied by the jaws 40 (FIG. 4) as the tissue cools. Cooling while the tissue is compressed allows the tissue fibers to intertwine and fuse together in a manner which resists separation. After the tissue has cooled at 228, the compression force or pressure on the sealed apposite portions of the sidewall 36 is released at 230 by opening the jaws 40 (FIG. 2) after having disengaged the teeth 60 of the tabs 58 (FIG. 1). Thereafter, the sequence 200 returns to 202 to await the beginning of another treatment cycle 66 (FIG. 5).

The present invention has been implemented by using a ConMed System 5000 electrosurgical generator as the electrosurgical generator 42 and both a handheld version and a 5 mm laparoscopic version of a ValleyLab Ligasure handpiece as the handpiece 38. The ConMed System 5000 electrosurgical generator was operated in a fluid bipolar mode. The advantage of using the fluid bipolar mode is that it has the capability of delivering a relatively high amount of power into a relatively low impedance tissue. This characteristic is advantageously used to deliver enough electrical energy into the compressed apposite portions of the sidewall 36 tissue to rapidly heat the sidewall portions during the initial heating phase 68 (FIG. 5). The fluid bipolar mode was originally intended to be used in arthroscopic surgery where the surgical site is totally immersed in water or saline. Because of the high conductivity and therefore low impedance of the water or saline, the boosted power capacity and lower internal source impedance in the fluid bipolar mode creates an added capability to quickly deliver energy, which is useful in the present invention to quickly heat the compressed apposite sidewall portions of the tissue.

By rapidly delivering the energy, relatively short total times for completing the entire tissue sealing treatment cycle 66 are achieved. Less thermal spread to the adjoining tissues occurs compared to that resulting from using a standard electrosurgical generator operated in the conventional cutting or coagulation mode of power delivery. The higher rate of energy delivery is accomplished in part by more closely matching the source impedance of the electrosurgical generator with the load impedance of the compressed apposite portions of the sidewall 36, thereby enhancing the energy transfer capability of the electrosurgical generator into low impedance tissue.

In implementing the invention, the ConMed System 5000 electrosurgical generator was set to deliver 90 watts of electrosurgical energy when used with the handheld Valleylab Ligasure handpiece. The ConMed System 5000 electrosurgical generator was set to deliver 70 watts of electrosurgical energy when used with the laparoscopic Valleylab Ligasure handpiece. The threshold value 82 was established at 1.0 amps (and the threshold level signals 116 and 118 (FIG. 7) were set correspondingly) and the threshold time 83 was established at 150 milliseconds. The duration of the energy completion time 88 was established at 980 milliseconds. These values were equally useful for sealing arteries and veins of a relatively small diameter up to approximately 12 mm in diameter. The threshold value, the threshold time and the energy completion time proved satisfactory for use with both versions of the Valleylab Ligasure handpiece.

Using the embodiment of the invention described in the immediately preceding paragraph, the experimental seal time for arteries and veins was about 3 to 5 seconds. The published times required for performing a single seal of a vessel using a popular prior art tissue sealing device is about the same, thereby demonstrating superiority or comparability of the present invention in regard to the time required to accomplish single tissue seals. However, the widely accepted practice of using the popular prior art tissue sealing device is to perform four separate seals, with two of the seals overlapped and with each pair of overlapped seals spaced longitudinally from one another along the length of the vessel, makes total sealing times in the neighborhood of approximately 20 seconds commonplace. Tests performed with the embodiment of the invention described above have demonstrated that a single seal is just as effective as the four repetitive seals performed with the popular prior art tissue sealing device. Mean burst pressures of a single seal on a vessel accomplished by use of the above described embodiment of the present invention are equal or somewhat greater than the mean burst pressures of a multiple seal on a comparable vessel accomplished by use of the popular prior art tissue sealing device.

Using the above-described embodiment of the invention resulted in transferring an average of approximately 35 watts of electrical power to the vessel, which is typically considerably less than the total energy delivered for sealing a comparable vessel by the popular prior art tissue sealing device. Applying less energy to achieve the same or better seal burst pressures results in less tissue damage. Healing time is shortened because of the lesser tissue damage.

Experiments were conducted using the above-described embodiment of the present invention to establish the optimum range for the threshold time 83. Setting the threshold time 83 at a value less than 100 milliseconds or greater than 200 milliseconds resulted in a significant number of ineffective tissue seals, when the threshold value was set at 1.0 amps. Optimal sealing conditions were obtained at approximately 150 milliseconds for the threshold time 83 with a threshold value of 1.0 amps. It is expected that adequate but not optimal sealing conditions will result from values of the threshold time 83 within the range of approximately 125 to 175 milliseconds with a threshold value of 1.0 amps.

The values for the threshold RF current, the threshold time and the energy completion time were established relative to the implemented form of the invention described above. These values may need to be adjusted for other types of electrosurgical generators depending on, among other things, the output energy delivery characteristics of the other generators, the source impedances of the other generators, the real or apparent power regulation characteristics of the other generators, the impedance of the handpieces used, and the type of tissue which is sealed. Note however, that no changes were required to the above-described embodiment of the invention when sealing a relatively wide range of different sized arteries and veins.

Despite anticipated changes according to different implementations of the present invention, the general approach of timing the termination point of the electrical energy delivered to the compressed apposite portions of the sidewall 36 based on sensing the peak RF current so as to not exceed the threshold value for the threshold time, and thereafter measuring an energy completion time relative to this precursor fusion condition, is expected to perform satisfactorily with any electrosurgical generator which has the capability of delivering relatively significant amounts of power in a relatively short time into relatively low impedances, such as those represented by the compressed apposite portions of the sidewall 36 of the tissue to be sealed, in combination with popular tissue sealing handpieces, when used on the typical types of tissues which are normally sealed during typical medical procedures.

Figure 16:
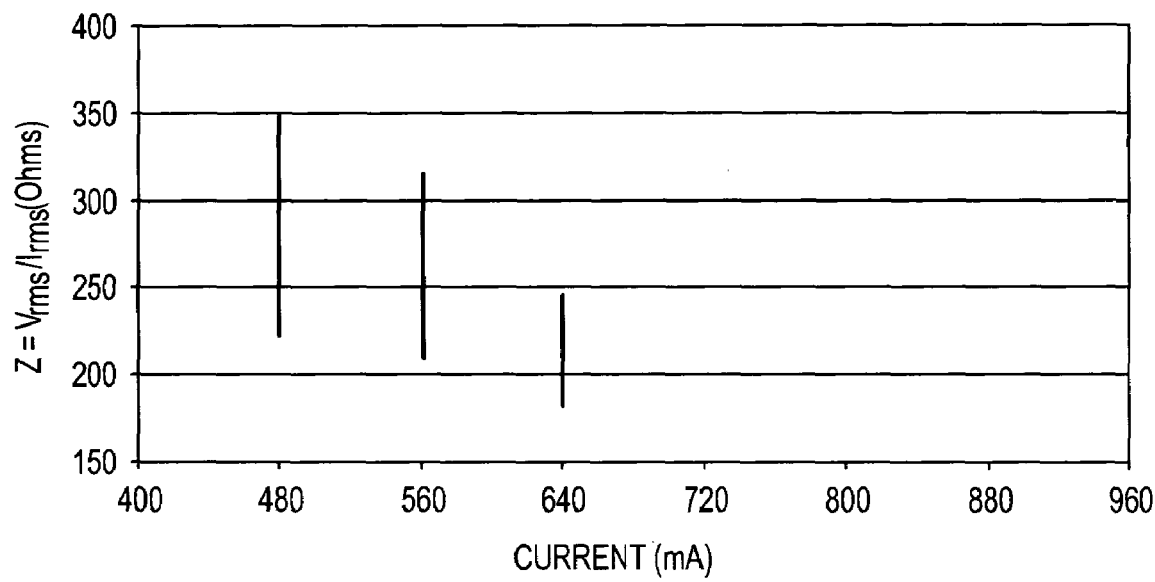
FIGS. 16, 17 and 18 are graphs of a range of impedances measured relative to certain current values shown in FIG. 6, during the execution of the tissue sealing treatment cycle.

The sealing capability by the present invention is obtained without resorting to complicated and expensive feedback power controls and impedance-related sensing techniques, as are prevalently used in prior art tissue sealing devices. Indeed, experiments have shown that the RMS impedance of the tissue varies considerably at the time of occurrence of the above-described precursor fusion condition. FIG. 16 shows the range of impedance which have been observed to occur relative to different values of RF current 64 when the precursor fusion condition is achieved, i.e. at point 86 (FIG. 6). Different values of RF current 64 have been observed because of the different types of tissue tested. The range of impedance at each of these precursor conditions indicates that a single impedance value does not correlate to the precursor condition, and therefore a single impedance value would not be a suitable replacement for determining the precursor fusion conditions for controlling the termination of electrical energy delivery when completing the tissue sealing treatment cycle 66.

Figure 17:
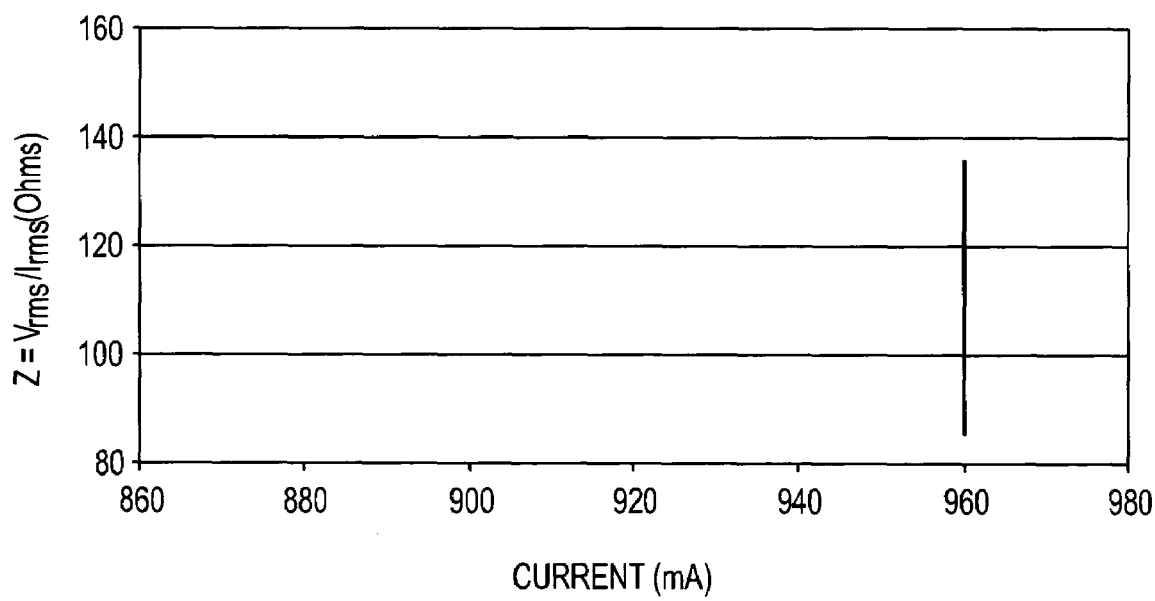
Figure 18:
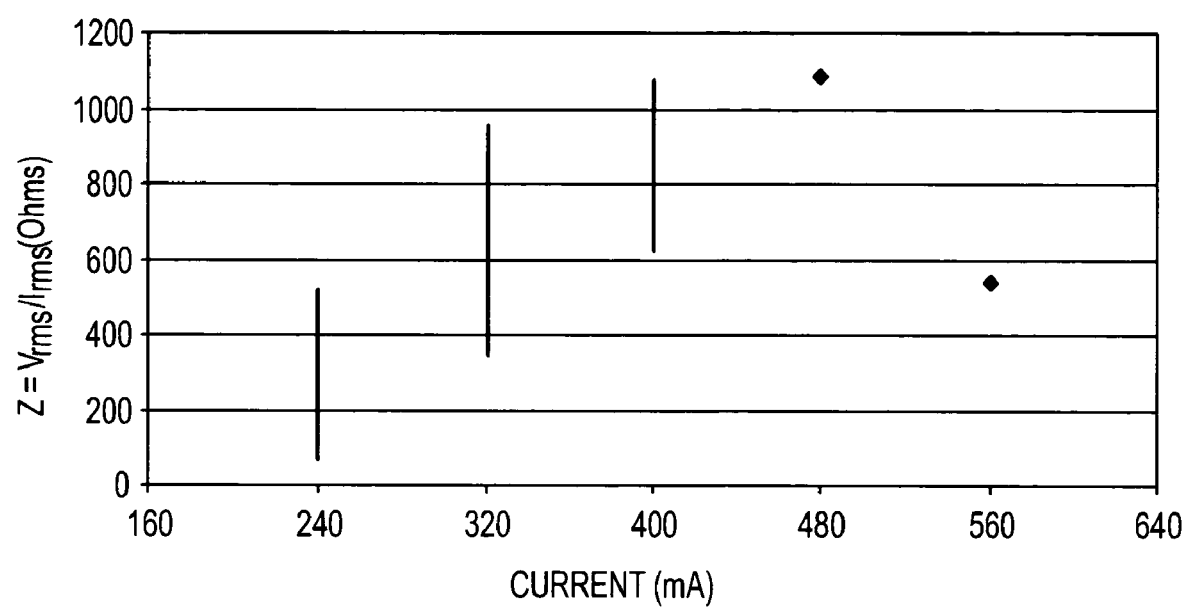

Furthermore, FIG. 17 illustrates that a wide range of impedances also exist at the start of determining the precursor fusion condition, i.e. at point 84 (FIG. 6). Lastly, FIG. 18 illustrates that a variety of different impedances also exist for each of the current values that were observed during tests at the energy delivery termination point 80 (FIG. 5). Accordingly, the impedance ranges shown in FIGS. 16-18 demonstrate that the precursor fusion condition determination made in accordance with the present invention does not correlate to the use of impedance values as are typically employed in prior art tissue fusion devices.

In the present invention, the electrosurgical generator 42 delivers the electrical energy in accordance with its normal functionality to obtain effective tissue sealing or fusion. The controller 46 senses the current to determine when the desired precursor fusion condition occurs. Thereafter only the additional energy is applied which is necessary to ensure an effective seal without weakening the tissue due to excessive energy application and without compromising the integrity of the seal by not delivering adequate energy. The functionality of the controller 46 greatly simplifies the tissue sealing process, since only straightforward threshold comparisons and timing determinations are used in relation to sensing the peak RF current 64. Many other advantages and improvements will be apparent upon gaining a full appreciation for the present invention.

A presently preferred embodiment of the invention and many of its improvements have been described above with a degree of particularity. The description is of the preferred example of implementing the invention, and is not necessarily intended to limit the scope of the invention. The scope of the invention is defined by the following claims.

The invention claimed is:

1. A tissue sealing apparatus for coaptively sealing a sidewall of biological tissue which surrounds and defines an opening in the tissue to occlude the opening permanently, comprising:

a handpiece having movable jaws to compress apposed portions of the sidewall with sufficient pressure for sealing the opening;

an electrical energy generator connected to the handpiece and operative to conduct sufficient electrical energy to the jaws and through the compressed apposed portions of the sidewall during a treatment cycle to fuse together permanently the apposed sidewall portions and permanently occlude the opening, the energy delivered from the generator includes RF current delivered in RF cycles, each RF cycle of the RF current having a peak current value, the treatment cycle having an initial heating phase during which the peak current values of the RF current cycles have initial peak current values and also having a reduction phase during which the peak current values of the RF current cycles diminish from the initial peak current values due to the desiccation of the tissue and an increase in the impedance of the tissue;

a controller connected to control the duration of the electrical energy conducted from the generator to the handpiece and through the compressed apposed sidewall portions to avoid inadequate and excessive energy application for coaptively sealing the tissue, the controller including:

a switch which is movable from a closed position to an opened position in response to a termination signal asserted to the switch, the closed position conducting the energy including the RF current from the generator to the handpiece, the opened position terminating the conduction of the energy from the generator to the handpiece;

a detector which includes a threshold circuit, a comparator and a threshold timer, the threshold circuit developing a threshold value which is less than the initial peak current values of RF current cycles during the initial heating phase, the comparator connected to the threshold circuit and comparing the peak current values of RF current cycles to the threshold value, the threshold timer establishing a predetermined threshold time duration, and wherein the detector delivers a trigger signal upon the peak current values of the RF current cycles not exceeding the threshold value for the predetermined threshold time; and an energy completion timer receptive of the trigger signal and operative to assert the termination signal to the switch upon expiration of a predetermined energy completion time measured from assertion of the trigger signal.

2. A tissue sealing apparatus as defined in claim 1, wherein:
the switch normally occupies the closed position.

3. A tissue sealing apparatus as defined in claim 1, wherein:
the initial heating phase comprises a multiple number of RF current cycles of substantially constant initial peak current values which heat the tissue; and
the reduction phase comprises a multiple number of RF current cycles of generally decreasing peak current values.

4. A tissue sealing apparatus as defined in claim 3, wherein:
the increase in tissue impedance during the reduction phase causes arcing of the electrical energy between the jaws; and
the threshold value and the predetermined threshold time duration cause the detector to deliver the trigger signal before arcing occurs.

5. A tissue sealing apparatus as defined in claim 3, wherein:
the increase in tissue impedance during the reduction phase causes arcing of the electrical energy between the jaws; and
the predetermined energy completion time causes assertion of the termination signal after arcing occurs.

6. A tissue sealing apparatus as defined in claim 1, wherein:
each RF current cycle has positive and negative peak current values;
the threshold circuit establishes a positive threshold value and a negative threshold value;
the comparator compares positive and negative peak current values of each RF current cycle to the positive and negative threshold values to determine whether the positive and negative peak current values of each RF current cycle exceed the positive and negative threshold values in a positive and negative sense, respectively; and
the detector delivers the trigger signal upon none of the positive and negative peak current values of the RF current cycles respectively exceeding the positive and negative threshold values in the positive and negative sense for the predetermined threshold time duration.

7. A tissue sealing apparatus as defined in claim 1, wherein:
the detector reinitiates use of the predetermined threshold time duration to determine the delivery of the trigger signal whenever the peak current value of one RF current cycle exceeds the threshold value.

8. A tissue sealing apparatus as defined in claim 1, wherein the controller further comprises:
a maximum duration timer which measures a delivery time that electrical energy is delivered from the generator to the handpiece and which asserts a control signal to the switch upon the delivery time exceeding a predetermined maximum time duration which is longer than an expected time duration of a normal treatment cycle; and wherein:
the switch moves to the opened position in response to the asserted control signal.

9. A tissue sealing apparatus as defined in claim 1, wherein the predetermined threshold time duration is in the range of 100 to 200 milliseconds.

10. A tissue sealing apparatus as defined in claim 1, wherein the predetermined threshold time duration is in the range of 125 to 175 milliseconds.

11. A tissue sealing apparatus as defined in claim 1, wherein the predetermined threshold time duration is approximately 150 milliseconds.

12. A tissue sealing apparatus as defined in claim 1, wherein the predetermined energy completion time is in the range of 900 to 1200 milliseconds.

13. A tissue sealing apparatus as defined in claim 1, wherein the predetermined energy completion time is approximately 980 milliseconds.

14. A controller which controls the duration of electrical energy conducted from an electrical energy generator to a handpiece and through compressed apposed sidewall portions of biological tissue to seal the sidewall portions and permanently occlude an opening previously defined by the sidewall portions while avoiding inadequate and excessive energy application for coaptively sealing the tissue, the handpiece having movable jaws which compress apposed sidewall portions with sufficient pressure for sealing the opening, the generator conducting RF current delivered in RF cycles to the jaws and through the compressed apposed sidewall portions during a treatment cycle, the RF current of each RF cycle having a peak current value, the treatment cycle having an initial heating phase during which the peak current values of the RF current cycles have initial peak current values and also having a reduction phase during which the peak current values of the RF current cycles diminish from the initial peak current values due to the desiccation of the tissue and an increase in the impedance of the tissue; the controller comprising:
a switch which is movable from a closed position to an opened position in response to a termination signal asserted to the switch, the closed position conducting the RF current from the generator to the handpiece, the opened position terminating the conduction of the RF current from the generator to the handpiece;
a detector which includes a threshold circuit, a comparator and a threshold timer, the threshold circuit developing a threshold value which is less than the initial peak current values of RF current cycles during the initial heating phase, the comparator connected to the threshold circuit and comparing the peak current values of RF current cycles to the threshold value, the threshold timer establishing a predetermined threshold time duration, and wherein the detector delivers a trigger signal upon the peak current values of the RF current cycles not exceeding the threshold value for the predetermined threshold time; and
an energy completion timer receptive of the trigger signal and operative to assert the termination signal to the switch upon expiration of a predetermined energy completion time measured from assertion of the trigger signal.

15. A controller as defined in claim 14, wherein:
the switch normally occupies the closed position.

16. A controller as defined in claim 14, wherein:
the initial heating phase comprises a multiple number of RF current cycles of substantially constant initial peak current values which heat the tissue; and
the reduction phase comprises a multiple number of RF current cycles of generally decreasing peak current values.

17. A controller as defined in claim 16, wherein:
the increase in tissue impedance during the reduction phase causes arcing of the electrical energy between the jaws; and
the threshold value and the predetermined threshold time duration cause the detector to deliver the trigger signal before arcing occurs.

18. A controller as defined in claim 16, wherein:
the increase in tissue impedance during the reduction phase causes arcing of the electrical energy between the jaws; and
the predetermined energy completion time causes assertion of the termination signal after arcing occurs.

19. A controller as defined in claim 14, wherein:
each RF current cycle has positive and negative peak current values;
the threshold circuit establishes a positive threshold value and a negative threshold value;
the comparator compares positive and negative peak current values of each RF current cycle to the positive and negative threshold values to determine whether the positive and negative peak current values of each RF current cycle exceed the positive and negative threshold values in a positive and negative sense, respectively; and
the detector delivers the trigger signal upon none of the positive and negative peak current values of the RF current cycles respectively exceeding the positive and negative threshold values in the positive and negative sense for the predetermined threshold time duration.

20. A controller as defined in claim 14, wherein:
the detector reinitiates use of the predetermined threshold time duration to determine the delivery of the trigger signal whenever the peak current value of one RF current cycle exceeds the threshold value.

21. A controller as defined in claim 14, wherein the controller further comprises:
a maximum duration timer which measures a delivery time that electrical energy is delivered from the generator to the handpiece and which asserts a control signal to the switch upon the delivery time exceeding a predetermined maximum time duration which is longer than an expected time duration of a normal treatment cycle; and wherein:
the switch moves to the opened position in response to the asserted control signal.

22. A controller as defined in claim 14, wherein the predetermined threshold time duration is in the range of 100 to 200 milliseconds.

23. A controller as defined in claim 14, wherein the predetermined threshold time duration is in the range of 125 to 175 milliseconds.

24. A controller as defined in claim 14, wherein the predetermined threshold time duration is approximately 150 milliseconds.

25. A controller as defined in claim 14, wherein the energy completion time is in the range of 900 to 1200 milliseconds.

26. A controller as defined in claim 14, wherein the energy completion time is approximately 980 milliseconds.

* * * * *